United States Patent [19]

Wang et al.

[11] 4,024,153

[45] May 17, 1977

[54] POLYCHROMOPHORIC BENZOTRIAZOLE ULTRAVIOLET STABILIZERS

[75] Inventors: Richard Hsu-Shien Wang; Gether Irick, Jr., both of Kingsport, Tenn.

[73] Assignee: Eastman Kodak Company, Rochester, N.Y.

[22] Filed: Dec. 10, 1975

[21] Appl. No.: 639,934

Related U.S. Application Data

[62] Division of Ser. No. 511,567, Oct. 2, 1974, Pat. No. 3,954,706.

[52] U.S. Cl. .......................................... 260/308 B
[51] Int. Cl.[2] .................................... C07D 249/20
[58] Field of Search ............................ 260/308 B

[56] References Cited

UNITED STATES PATENTS 3,766,205  10/1973  Heller et al. .................. 260/308 B Primary Examiner—Paul M. Coughlan, Jr.
Attorney, Agent, or Firm—Elliott Stern; Daniel B. Reece, III

[57] ABSTRACT

The invention relates to polychromophoric compounds which have been found to be effective ultraviolet stabilizers. The invention also relates to ultraviolet degradable organic compositions containing a stabilizing amount of the polychromophoric composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

20 Claims, No Drawings

POLYCHROMOPHORIC BENZOTRIAZOLE ULTRAVIOLET STABILIZERS

This is a division of application Ser. No. 511,567 filed Oct. 2, 1974, now U.S. Pat. No. 3,954,706.

This invention relates to polychromophoric ultraviolet stabilizers and their use in organic compositions. More particularly, the invention relates to polychromophoric compositions and the stabilization of ultraviolet degradable organic compositions against deterioration resulting from the exposure to such radiations with such polychromophoric compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be on advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing polychromophoric compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations, including short wavelength visible radiations.

Further objects and advantages of the invention will be apparent to those skilled in the art from the accompanying disclosure and claims.

In accordance with the present invention, polychromophoric compositions are provided which are useful as ultraviolet stabilizers or ultraviolet screening agents. These organic compositions contain at least one heterocyclic group containing composition connected through a carboxyl group to an aromatic ring which, upon exposure to ultraviolet light, may undergo the "photo-Fries" rearrangement. The polychromophoric compositions of the present invention have the following structure:

$$(A)_{\overline{x}}C$$

wherein A is a group having the structure

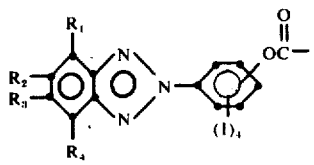

wherein $R_1$, $R_2$, $R_3$ and $R_4$ are hydrogen, lower alkyl or substituted lower alkyl having 1 to 12 carbon atoms, cycloalkyl, substituted cycloalkyl, aryl or substituted aryl having 6 to 18 carbon atoms, lower alkylaryl, aryl-substituted-aryl, chloro, bromo, fluoro, alkoxy and substituted alkoxy containing 1 to 12 carbon atoms, aryloxy, disubstituted amino, cyano, carboalkoxy and the substituents $R_1$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$.

I is a substituent listed above for $R_1$, $R_2$, $R_3$ and $R_4$ and is present on all positions of the benzenoid ring, except the carbon atom attached to the N substituent and the carbon atom attached to the carbonyl group. The carbonyl connecting group is attached to the benzenoid ring in the ortho, meta or para position from the carbon atom connected to the heterocyclic ring. At least one I attached to a carbon atom adjacent to the carbon atom attached to the carbonyl group is hydrogen. The other I substituents can all be one of the substituents listed above or different listed substituents; x is an integer of 1 to 6, preferably 1 to 3;

C is an aromatic moiety having the formula

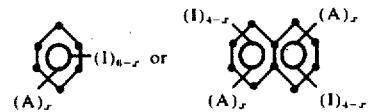

I is the same substituent as listed above and is present in all positions of the benzenoid ring except the carbon atom attached to the carbonyl group connecting the A and C moieties. The A moiety is attached to the benzenoid ring in from 1 to 6 positions. If two A moieties are attached to the C moiety they can be attached in the ortho, meta or para position from each other. If three or four A moieties are attached to the C moiety they can be attached in the ortho or meta positions from each other. It is necessary that at least one I substituent to the carbon atom attached to the carbonyl group be hydrogen so that, on exposure to ultraviolet light, the aryl ester of heterocyclic aromatic acid is capable by the "photo-Fries" rearrangement of forming a phenol group in that position formerly joined through an oxygen atom to the carbonyl linking group. The remaining T substituent can all be one of the substituents listed above or different listed substituents.

Suitable heterocyclic A groups having the structure

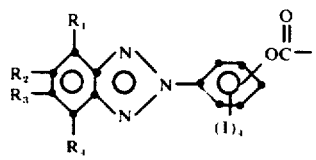

are for example substituted and unsubstituted benzotriazoles such as 4-(5-chloro-2H-benzotriazol-2-yl)phenoxycarbonyl, 4-(2H-benzotriazol)-2-yl)phenoxycarbonyl, 4-(5-methoxy-2H-benzotriazol-2-yl)phenoxycarbonyl, 2,5-dimethyl-4-(2H-benzotriazol-2-yl)phenoxycarbonyl, 2,5-dimethyl-4-(5-chloro-2H-benzotriazol-2-yl)phenoxycarbonyl, 2-methyl-4-(2H-benzotriazol-2-yl)phenoxycarbonyl, 2-chloro-4-(2H-benzotriazol-2-yl)phenoxycarbonyl, 2,5-dichloro-4-(2H-benzotriazol-2-yl)phenoxycarbonyl, 2-chloro-4-(5-chloro-2H-benzotriazol-2-yl)phenoxycarbonyl, 2,6-dichloro-4-(5-chloro-2H-benzotriazol-2-yl)phenoxycarbonyl, 2,6-dimethyl-4-(5-methoxy-2H-benzotriazol-2-yl)phenoxycarbonyl, 2,6-dichloro-4(5-methoxy-2H-benzotriazol-2-yl)phenoxycarbonyl, 2-chloro-4-(5-methoxy-2H-benzotriazol-2yl)phenoxycarbonyl, 2-methyl-4-(5-methoxy-2H-benzotriazol-2-yl)phenoxycarbonyl, 2-phenyl-4-(2H-benzotriazol-2-yl)phenoxycarbonyl, 2-phenyl-4-(5-chloro-2H-benzotriazol-2-yl)phenoxycarbonyl, 2-phenyl-4-(5-methoxy-2H-benzotriazol-2-yl)phenoxycarbonyl, 4-(4,6-dichloro-2H-benzotriazol-2-yl)phenoxycarbonyl, 4-(4,6-dimethyl-2H-benzotriazol-2-yl)phenoxycarbonyl, and the like.

Suitable C moieties having the formula

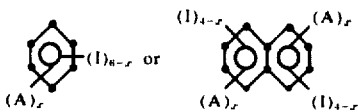

are for example, phenyl, benzen-1,2-diyl, benzen-1,3-diyl, benzen-1,4-diyl, benzen-1,2,4-triyl, benzen-1,3,5-triyl, benzen-1,2,3-triyl, benzen-1,2,4,5-tetrayl, 4-cyanophenyl, 2,4-dimethylphenyl, 3-methoxyphenyl, 2,4-dichlorophenyl, 4-benzoylphenyl, 4-bromo-2-chlorophenyl, 2-bromobenzen-1,4-diyl, 4-methoxybenzen-1,2-diyl, 2,5-difluorobenzen-1,4-diyl, 4-phenoxyphenyl, 4-acetamidophenyl, (4-(2-benzoxazolyl)phenyl, and 4-(2-benzthiazolyl)phenyl), 1,2-dinaphthoyl, 1,3-dinaphthoyl, 1,4-dinaphthoyl, 1,5-dinaphthoyl, 1,6-dinaphthoyl, 1,7-dinaphthoyl, 1,8-dinaphthoyl, 2,6-dinaphthoyl, 2,7-dinaphthoyl, 2,8-dinaphthoyl, 5-methoxy-1,2-dinaphthoyl, 5-chloro-1,2-dinaphthoyl, 6-methoxy-1,3-dinaphthoyl, 4-chloro-1,8-dinaphthoyl, 6,7-dimethyl-1,4-dinaphthoyl, 8-methoxy-1,3-dinaphthoyl, 1,2,5,6-tetranaphthoyl, 1,4,5,8-tetranaphthoyl, 2,4,6-trinaphthoyl, 1,3,5-trinaphthoyl, and the like.

The polychromophoric compositions can be prepared by reacting with an an aroyl chloride phenol. For example, one group of such organic compounds useful as ultraviolet stabilizers is, for example, compositions having the following structure

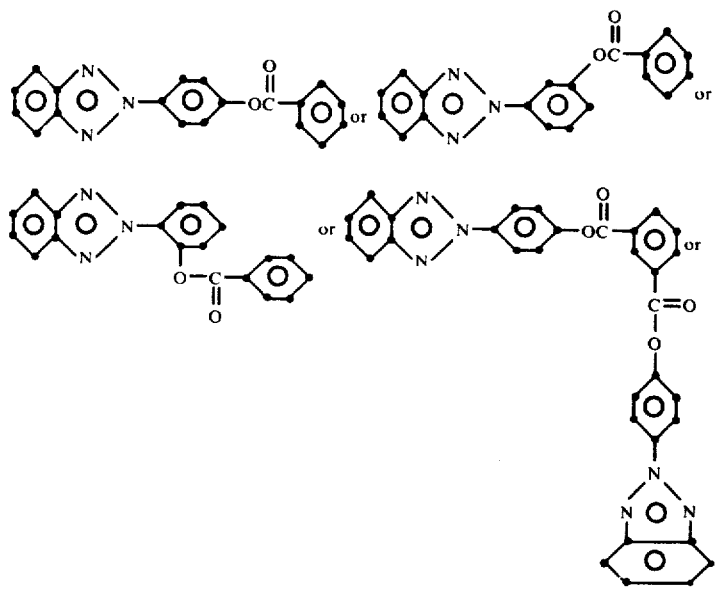

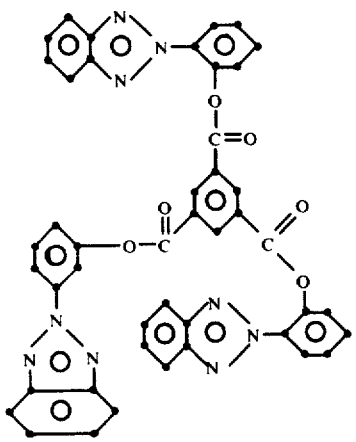

One method for preparing these compounds is by the following procedure:

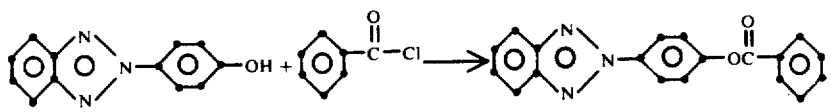

It is necessary that at least one carbon atom adjacent to the carbon atom attached to the carbonyl group contain a hydrogen substituent so that on exposure to ultraviolet light, the aryl ester is capable by the "photo-Fries" rearrangement of forming a phenol group in that position formerly joined through an oxygen atom to the carbonyl linking group, as for example:

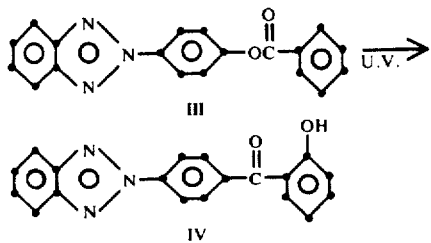

The heterocyclic compositions can be added to organic compositions which are susceptible to ultraviolet degradation. Such compositions include, for example, polymeric compositions such as polyester fiber and molding compositions, such as polyethylene terephthalate, poly(tetramethylene terephthalate) and the like; polyolefins such as, for example, high, medium and low density polyethylene, polypropylene, polybutene and the like; polyamides such as nylon 6, nylon 66, N-methoxymethyl polyhexamethylene adipamide and the like; polycarbonates; polyvinyl chlorides and copolymers; cellulose esters; acrylic/butadiene/styrene plastic; polyacrylics such as methyl methacrylate polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The polychromophoric compositions, as effective ultraviolet stabilizers or screening agents, are generally used in an amount of from 0.01 to 10%, by weight based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate and polyester such as poly(tetramethylene terephthalate) plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel polychromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

Preparation of p-(2H-benzotriazol-2-yl)phenylbenzoate (I) can be prepared by the following procedure:

o-Nitroaniline (0.5 mole) was diazotized in the usual manner with concentrated hydrochloric acid (200 ml.) and sodium nitrite (0.5 mole). The clear diazonium solution was added slowly to a cold solution (0°–5° C.) of phenol (0.5 mole) in 450 ml. of 10% sodium hydroxide. The mixture was stirred for 1 hour and Compound A filtered out (60% yield). One-tenth mole of Compound A was dissolved in 100 ml. of 2N NaOH. Zinc dust (30 g.) and sodium hydroxide (50 ml. of a 25% solution) were added slowly to the well-stirred solution to keep the temperature below 45° C. The mixture was then cooled to <30° C. and acidified with concentrated hydrochloric acid. After stirring for 2 hours, the precipitate was filtered. Compound B was recrystallized from ethanol-water (m.p. 216–8° C., 90% yield). To the stirred solution of Compound B (0.02 mole) in 50 ml. of 1.6% sodium hydroxide, benzoyl chloride (0.02 mole) in 50 ml. of chloroform was added slowly. The mixture was refluxed for 2 hours. The organic layer was separated and washed with water. After removal of chloroform by evaporation, compound (I) was obtained. The product, I, was purified by crystallization from ethanol. (Yield: 80%, m.p. 164–6° C.). Anal. Calcd. for $C_{19}H_{13}N_3O_2$: C, 72.48 H, 4.27; N, 13.53. Found C, 72.37; H, 4.16; N, 13.13.

procedure described for I, (m.p. 290–2° C., yield 90%). Anal. calcd. for $C_{32}H_{20}N_6O_4$; C, 68.97; H, 3.95; N, 15.25. Found: C, 69.56; H, 3.65; N, 15.21.

EXAMPLE 4

Tris[p-(2H-benzotriazol-2-yl)phenyl] 1,3,5-benzenetricarboxylate (IV) can be prepared by reaction of p-(2H-benzotriazol-2-yl)phenol with 1,3,5-benzenetricarboxylic acid chloride as in the procedure described for I, (m.p. 305°–310° C., yield, 80%). Anal

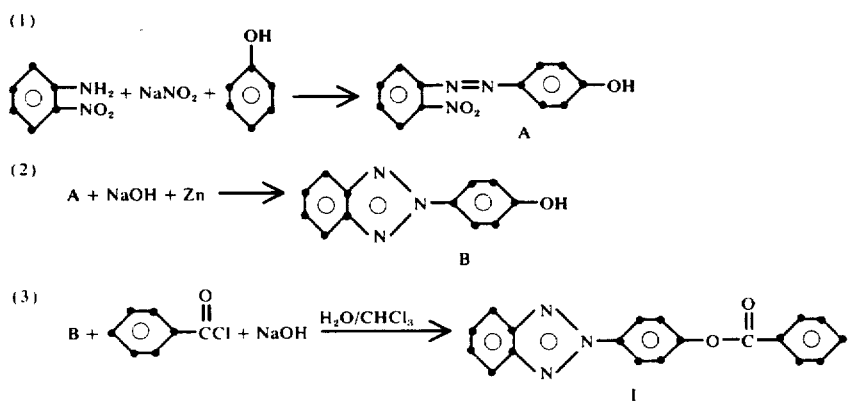

Other novel polychromophoric compounds can be prepared by substitution of other benzotriazoles for 4-(2H-benzotriazol-2-yl)phenol, such as 4-(5-chloro-2H-benzotriazol-2yl)-2,5-dimethylphenol, 4-(5-chloro-2H-benzotriazol-2-yl)phenol, 4-(5-methyl-2H-benzotriazol-2-yl)-2,5-dimethylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-f2-chlorophenol, 4-(5-chloro-2H-benzotriazol-2-yl)-2-chlorophenol, 4-(5-methyl-2H-benzotriazol-2-yl)-2-chlorophenol, 4-(2H-benzotriazol-2-yl)-2,5-dimethoxyphenol, 4-(5-chloro-2H-benzotriazol-2-yl)-2,5-dimethoxyphenol, 4-(5-methyl-2H-benzotriazol-2-yl)-2,5-dimethoxyphenol, 4-(2H-benzotriazol-2-yl)-2-methoxyphenol, 4-(5-chloro-2H-benzotriazol-2-yl)-2-chlorophenol, and 4-(5-methyl-2H-benzotriazol-2-yl)-2-methoxyphenol.

Also, either polychromophoric compounds can be prepared by substituting other aroyl chlorides for benzoyl chloride such as 2,4-dichlorobenzoyl chloride, 2,4-dimethoxybenzoyl chloride, 4-n-butoxybenzoyl chloride, terephthaloyl chloride, 3-cyanobenzoyl chloride, isophthaloyl chloride, 1,3,5-benzenetricarboxylic acid chloride, phthaloyl chloride, 2-bromoterephthaloyl chloride, 2,5-dimethoxyterephthaloyl chloride, 4-(2-benzoxazolyl)benzoyl chloride and 4-(2-benzthiazoyl)benzoyl chloride.

EXAMPLE 2

Bis-[p-(2H-benzotriazol-2-yl)phenyl terephthalate (II) can be prepared by the reaction of p-(2H-benzotriazol-2-yl)phenol with terephthaloyl chloride as in the procedure described for I, m.p. >300° C., yield 75%. Anal. calcd. for $C_{32}H_{20}N_6O_4$: C, 68.32; H, 3.86; N, 15.09. Found: C, 69.56; H, 3.65; N, 15.21.

EXAMPLE 3

Bis-[p-(2H-benzotriazol-2-yl)phenyl] isophthalate (III) can be prepared by reaction of p-(2H-benzotriazol-2-yl)phenol with isophthaloyl chloride as in the calcd. for $C_{45}H_{27}N_9O_6$; C, 68.24; H, 3.60; N, 15.52. Found: C, 68.44; H, 3.45; N, 15.96.

EXAMPLE 5

The ultraviolet stabilization provided by the heterocyclic compound of the present invention is shown for poly(tetramethylene terephthalate) in Table 1.

A dry mixture of the stabilizer and granulated poly(tetramethylene terephthalte) was extruded into 1/16-inch diameter rods, pelletized and injection molded into 2½- × ½- × 1/16-inch flat bars; these flat bars were exposed to a 280–700 nm. mercury lamp source.

The test results are summarized in Table 1.

Table I

| | Effectiveness of Ultraviolet Stabilizers in Poly(tetramethylene terephthalate) | | |
|---|---|---|---|
| | FWIS (Flatwise Impact Strength) | | |
| Compound (0.5%) | Initial | 500 hr. | 1000 hr. |
| None | 17 | 1 | 1 |
| I | 19 | 20 | 14 |
| II | 19 | 20 | 20 |
| III | 19 | 20 | 19 |
| IV | 19 | 20 | 18 |

These polychromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. Compound having the formula:

(A)ₐ—Z wherein A is a group having the structure

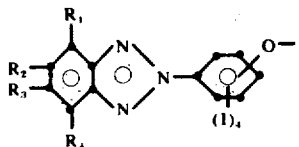

wherein the oxy group is in the meta or para position to the benzotriazole group;

$R_1$, $R_2$, $R_3$ and $R_4$ are hydrogen, chloro, bromo, fluoro, alkyl having 1 to 12 carbon atoms, cycloalkyl, phenyl, benzyl, alkoxy having 1 to 12 carbon atoms, cyano, and carboalkoxy having 2 to about 12 carbon atoms;

I is the same as $R_1$, $R_2$, $R_3$ and $R_4$ and is present on all positions of the benzenoid ring, except the carbon atoms attached to the heterocyclic ring and the carbon atom attached to the carbonyl group connecting the heterocyclic aromatic A group with the aromatic Z group, at least one I substituent on one of the carbon atoms adjacent to said carbon atom attached to said carbonyl group is hydrogen and said remaining I substituents can all be the same or different;

a is an integer of 1 to 4; and

Z is an aromatic group having the formula:

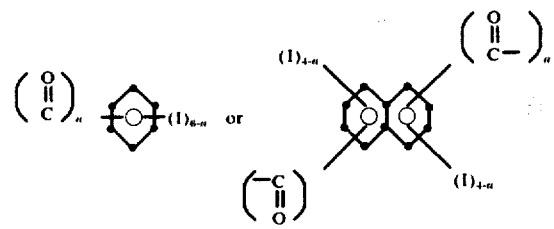

where I is the same substituent as listed above and is present in all positions of the benzenoid ring except the carbon atoms attached to the carbonyl group connecting the A and Z moieties, and said I substituents can all be one of the substituents listed above or different listed substituents.

2. Compound according to claim 1 having the formula:

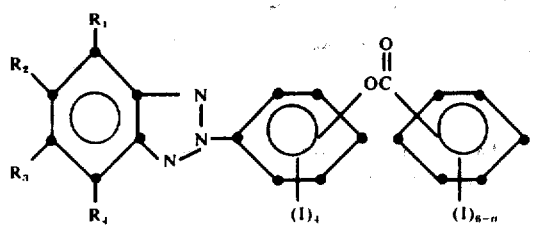

wherein the ester linking group is in the meta or para position to the benzotriazole group;

a is an integer of 2 to 4;

$R_1$, $R_2$, $R_3$ and $R_4$ are hydrogen, chloro, bromo, lower alkyl having 1 to 12 carbon atoms, cycloalkyl, phenyl, benzyl, alkoxy having 1 to 12 carbon atoms, aryloxy, cyano and carboalkoxy having 1 to 12 carbon atoms;

I is the same as $R_1$, $R_2$, $R_3$ and $R_4$ and is present on all positions of the benzenoid ring, except the carbon atom attached to the carbonyl linking substituent, at least one of said I substituents on one of the carbon atoms adjacent to said carbon atom attached to said carbonyl group is hydrogen and the remaining I substituents can all be one of the substituents listed above or different listed substituents.

3. A composition of matter according to claim 2 having the formula:

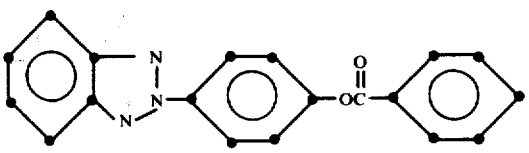

4. A composition of matter according to claim 2 having the formula:

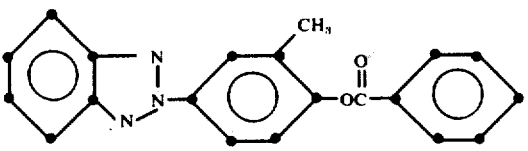

5. A composition of matter according to claim 2 having the formula:

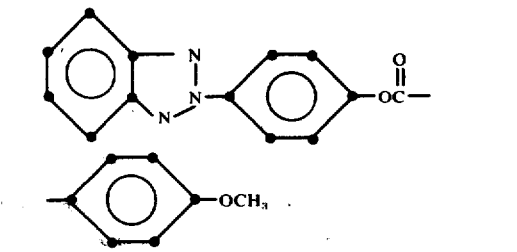

6. A composition of matter according to claim 1 having the formula:

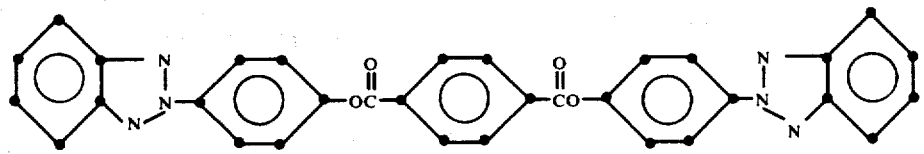

7. A composition of matter according to claim 2 having the formula:

8. A composition of matter according to claim 1 having the formula:

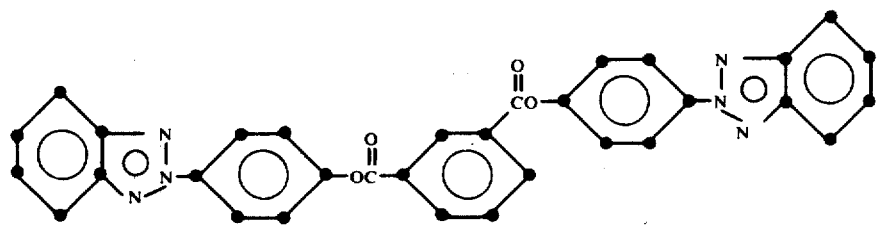

9. A composition of matter according to claim 1 having the formula:

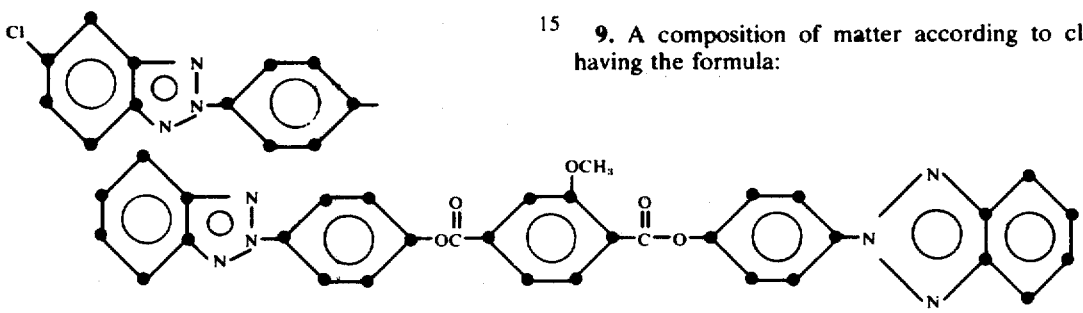

10. A composition of matter according to claim 1 having the formula:

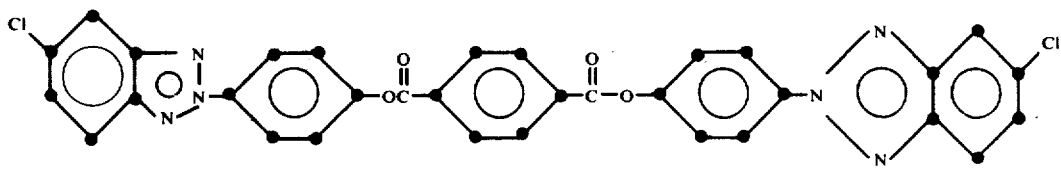

11. A composition of matter according to claim 1 having the formula:

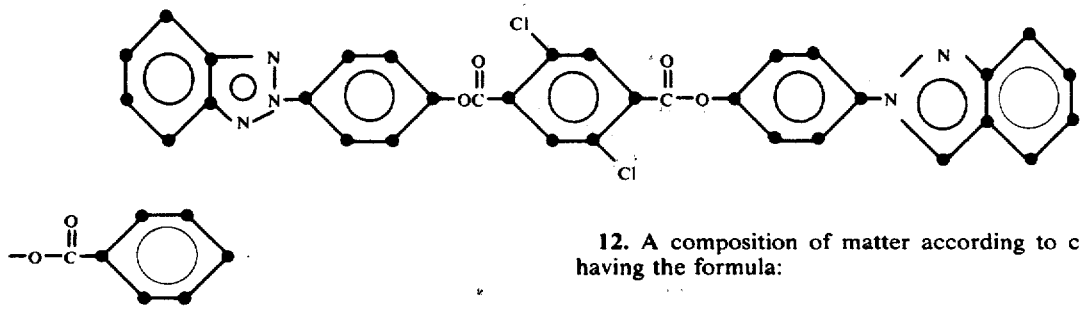

12. A composition of matter according to claim 1 having the formula:

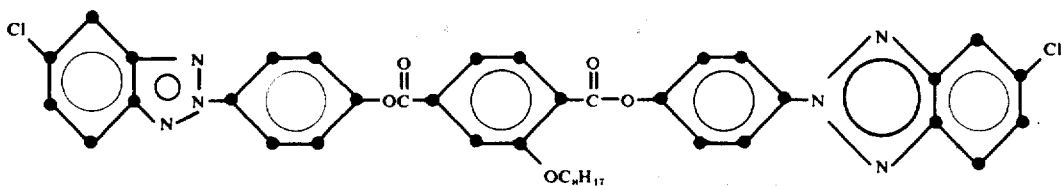

13. A composition of matter according to claim 1 having the formula:

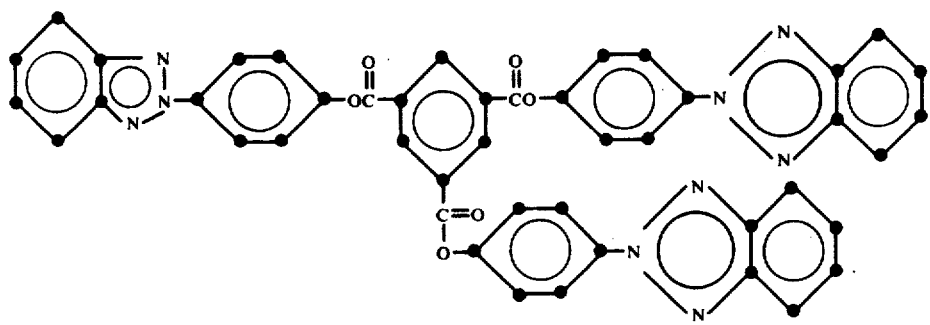

14. A composition of matter according to claim 2 having the formula:

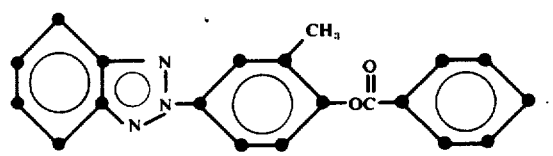

15. A composition of matter according to claim 2 having the formula:

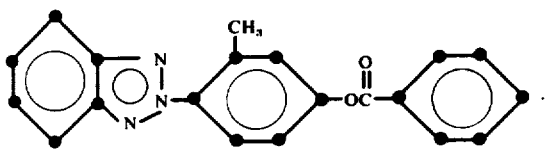

16. A composition of matter according to claim 2 having the formula:

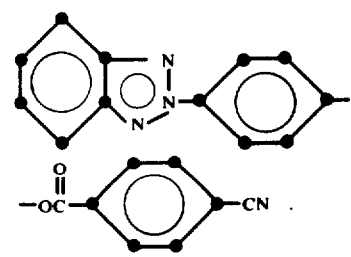

17. A composition of matter according to claim 2 having the formula:

-continued

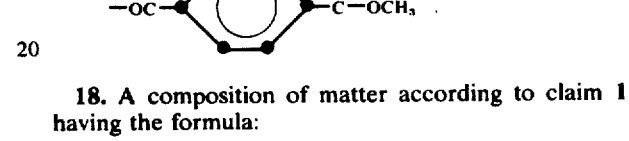

18. A composition of matter according to claim 1 having the formula:

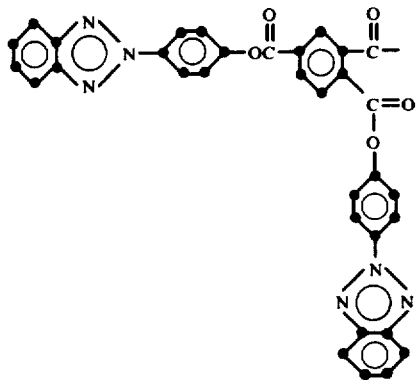

19. A composition of matter according to claim 2 having the formula:

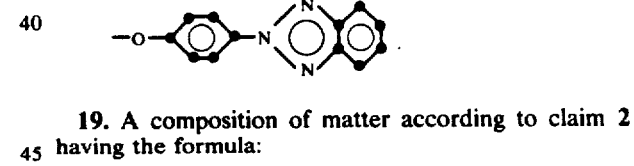

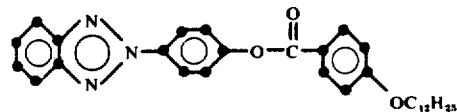

20. A composition of matter according to claim 1 having the formula:

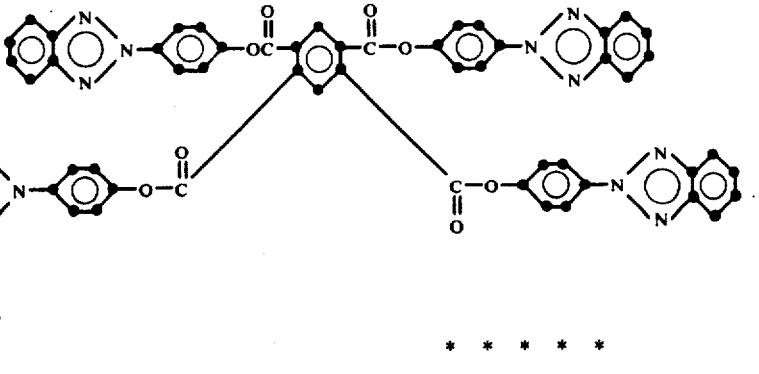

* * * * *